United States Patent [19]

Donnelly

[11] 4,437,062
[45] Mar. 13, 1984

[54] EDDY CURRENT TESTING APPARATUS INCLUDING A TWO COIL PROBE HAVING SANDWICHED WINDINGS

[75] Inventor: Bernard J. Donnelly, Kirkton, Scotland

[73] Assignee: Thorburn Technics (International) Limited, Glasgow, Scotland

[21] Appl. No.: 212,422

[22] Filed: Dec. 3, 1980

[30] Foreign Application Priority Data

Dec. 7, 1979 [GB] United Kingdom ............... 7942263
Sep. 15, 1980 [GB] United Kingdom ............... 8029772

[51] Int. Cl.³ ............... G01N 27/90; G01R 33/12; H01F 27/28
[52] U.S. Cl. ............... 324/238; 324/243; 336/183
[58] Field of Search ............... 324/228, 232, 234, 237, 324/238, 240, 242, 243; 336/170, 172, 180–183, 185, 186, 208, 220

[56] References Cited

U.S. PATENT DOCUMENTS

| | | | |
|---|---|---|---|
| 2,558,566 | 6/1951 | Jorgensen | 336/183 X |
| 2,957,129 | 10/1960 | Irwin | 324/238 |
| 2,980,848 | 4/1961 | Datt et al. | 324/238 |
| 3,371,272 | 2/1968 | Stanton | 324/243 X |
| 3,586,964 | 6/1971 | Strauch | 324/234 |
| 3,753,096 | 8/1973 | Wiers . | |
| 3,864,638 | 2/1975 | Audenard . | |
| 3,895,290 | 7/1975 | Audenard . | |
| 4,078,201 | 3/1978 | Buser . | |
| 4,088,953 | 5/1978 | Sarian | 324/238 X |

FOREIGN PATENT DOCUMENTS

| | | |
|---|---|---|
| 2338628 | 2/1974 | Fed. Rep. of Germany . |
| 2339496 | 2/1974 | Fed. Rep. of Germany . |
| 2309889 | 8/1974 | Fed. Rep. of Germany . |
| 2530723 | 1/1977 | Fed. Rep. of Germany . |
| 55-43420 | 3/1980 | Japan ............... 324/238 |

*Primary Examiner*—Gerard R. Strecker
*Attorney, Agent, or Firm*—Murray Schaffer

[57] ABSTRACT

An eddy current inspection probe includes a bobbin housing a central ferrite rod. Two coils are wound around one end of the ferrite rod. The coils form two legs of a bridge circuit driven at 1.5 to 2.0 MHz. Defects are located by detecting phase shift in the bridge output.

9 Claims, 6 Drawing Figures

EDDY CURRENT TESTING APPARATUS INCLUDING A TWO COIL PROBE HAVING SANDWICHED WINDINGS

DESCRIPTION

This invention relates to apparatus for materials inspection using an eddy current technique.

It is known to inspect for surface defects in metals by passing over the test piece a probe in the form of a coil which is supplied with an alternating current of a given frequency. When the probe is moved across a defect such as a crack, the eddy currents produced in the test piece cause a phase shift between the current in the probe and the supply. This phase shift can be detected and used to signal the presence of a defect.

However, the apparatus known hitherto has suffered from the disadvantage that the phase shaft varies with the direction of motion of the probe relative to the defect. In the extreme case, a known probe may fail to detect the presence of an elongate crack when the motion of the probe is along the length of the crack.

Another disadvantage of known probes is that they fail to distinguish, or to distinguish adequately, between the encountering of a defect and "lift-off", that is movement of the probe away from the surface of the test piece. A particular feature of this disadvantage is that known eddy current probes cannot be used to inspect welds in the as-welded condition because of the varying degrees of lift-off caused by the surface roughness of the weld.

One object of the present invention is to overcome or mitigate these problems and to provide an eddy current inspection probe which is insensitive to the relative motion between it and a defect and to lift-off.

The invention accordingly resides in an eddy current inspection probe, including a ferrite rod and a coil assembly, the coil assembly being positioned adjacent one end of the ferrite rod and comprising two overlapping coils.

The invention is particularly, but not exclusively, of use in the inspection of underwater structures, such as oil rigs. Thus, in the preferred form of the invention the probe includes a waterproof housing in which the coils and the ferrite rod are received.

Preferably, the housing is formed to provide a front face at a given distance axially from one end of the ferrite rod, whereby the front face can be pressed against the test piece to provide a stand-off gauge.

An embodiment of the invention will now be described, by way of example, with reference to the accompanying drawings, in which.

Figure 1:
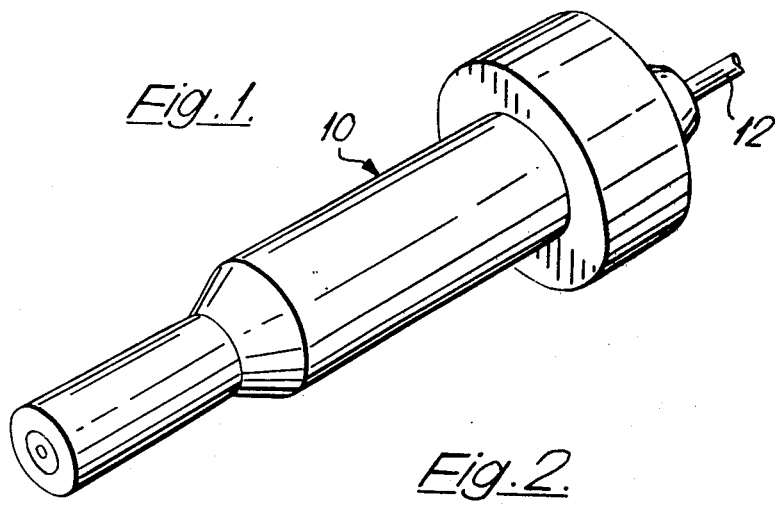
FIG. 1 is a perspective view of an eddy current inspection probe embodying the invention.
Figure 2:
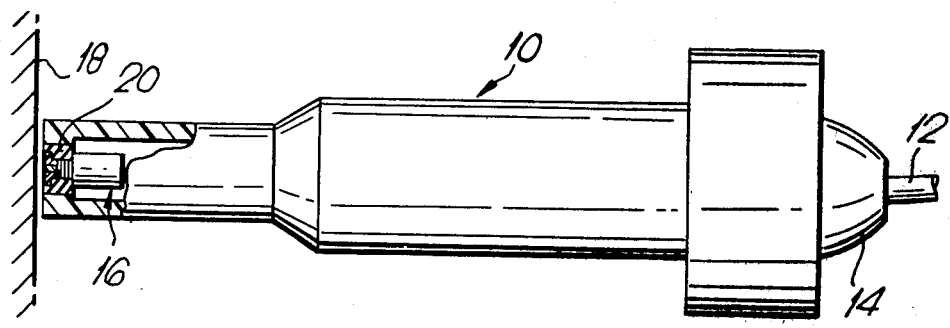
FIG. 2 is a side view, partly in section, of the probe of FIG. 1.

Referring particularly to FIGS. 1 and 2, the probe comprises a body 10 moulded from "Tufnol" or other suitable plastics material. A signal cable 12 is connected to the probe by a waterproof plug and socket indicated at 14. A bobbin assembly 16 is mounted at the front of the probe so that in use the bobbin assembly 16 will be closely adjacent a surface 18 to be inspected by moving the probe thereover. The bobbin assembly 16 may be secured in the body 10 by silicon rubber 20 which also acts as a seal.

Figure 3:
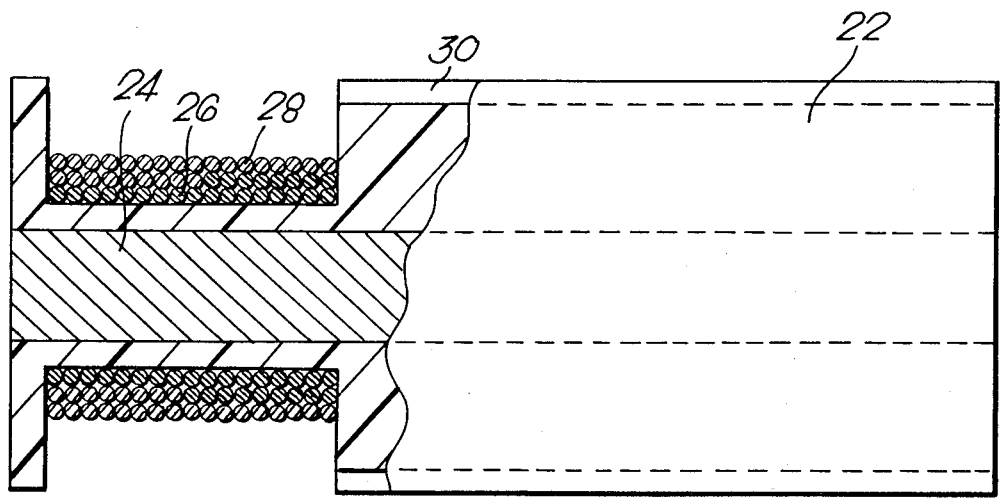
FIG. 3 is a side view, to an enlarged scale, of part of the probe.
Figure 4:
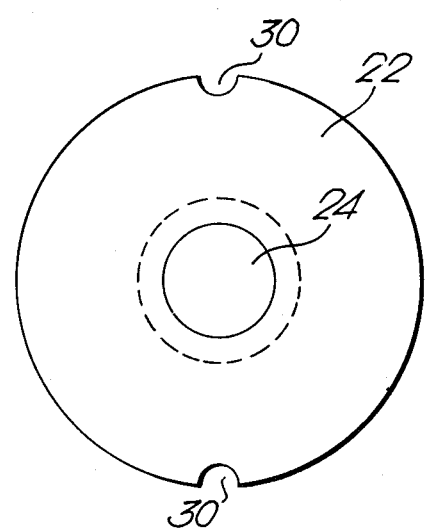
FIG. 4 is an end view corresponding to FIG. 3.

The bobbin assembly 16 is shown in greater detail in FIGS. 3 and 4. A bobbin 22 of "Tufnol" or other suitable plastics material has a central bore in which is received a ferrite rod 24. Grooves 30 are provided for engagement with ribs or studs (not shown) in the body 10. On the forward part of the bobbin are wound a first coil 26 and a second coil 28, each of enamelled copper wire. The coils are suitably each of 1½ layers of turns. As seen in FIGS. 3 and 4, the coils 26,28 are essentially located adjacent one end of the ferrite rod 24.

Figure 6:
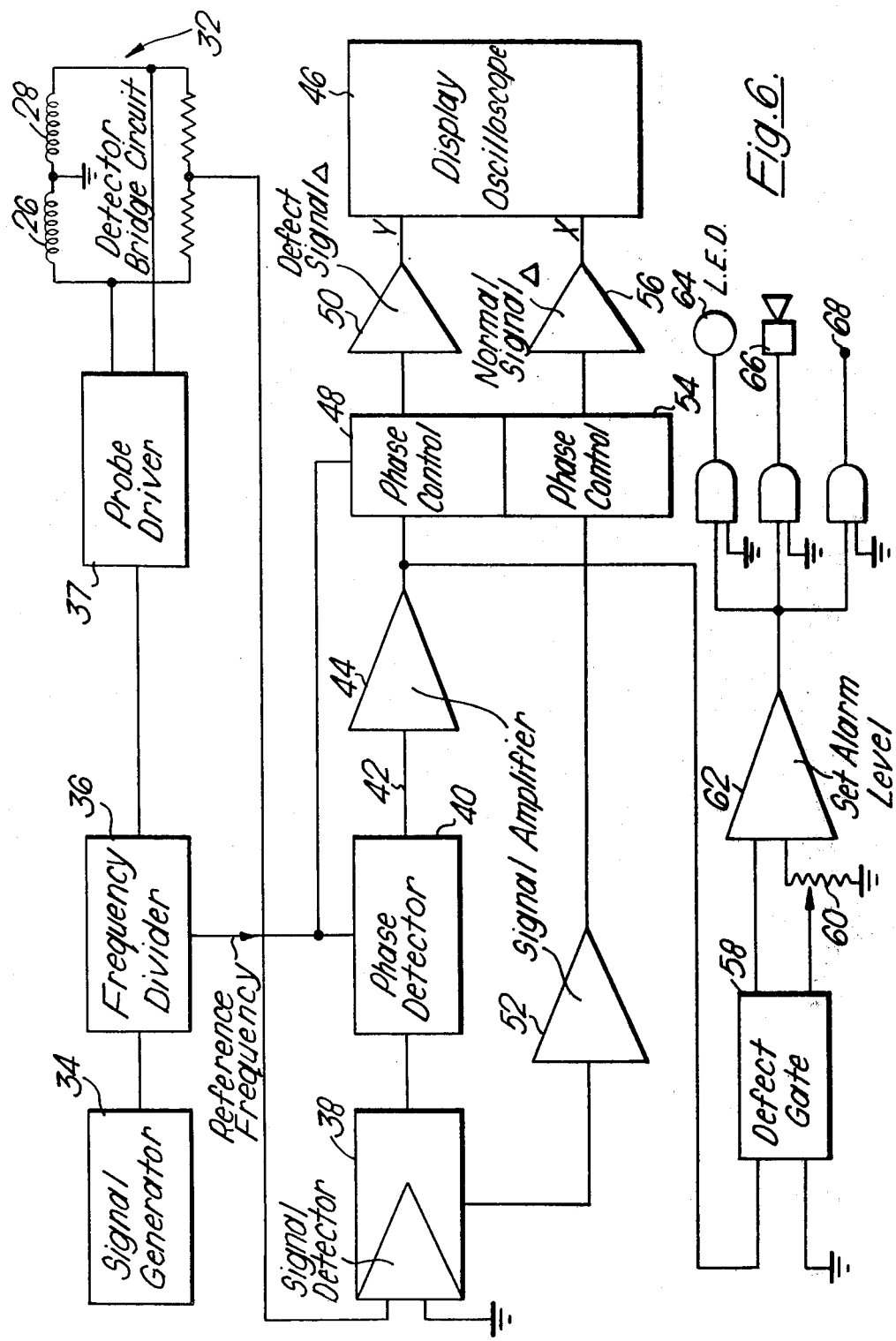
FIG. 6 is a block diagram of the circuitry associated with the probe in use.

Referring to FIG. 6, the coils 26 and 28 are connected in an a.c. bridge circuit 32. The bridge circuit 32 is driven at a given frequency derived from a signal generator 34 and frequency divider 36 via a driver amplifier 37.

The output of the bridge circuit 32 is applied to a signal detector 38 in which the phase and voltage of the bridge output signal are separated into phase and voltage signals. A phase detector 40 receives the phase signal and a reference phase signal from the frequency divider 36, and generates an output on line 42 whose amplitude is a function of the detected phase difference. The output on line 42 is amplified at 44 and applied to the Y-deflection of an oscilloscope 46 via a phase control circuit 48 and a driving amplifier 50. The voltage signal from the signal detector 38 is amplified at 52 and applied to the X-deflection of the oscilloscope 46 via a phase control circuit 54 and driving amplifier 56.

It has been found that with the probe of the invention, movement of the probe across a crack or similar defect gives rise to a phase shift, whereas relative movement of the probe toward and away from the bulk metal produces mainly a change in voltage. Thus movement of the probe across a rough test piece produces a substantially horizontal deflection on the oscilloscope but when a defect is encountered a clear vertical deflection is produced. The phase controls 48,54 provide fine adjustment to rotate these deflections, since on some metals the vectors produced are not completely perpendicular.

The circuitry of FIG. 6 also includes yes/no defect discriminating means. The phase-dependent signal from the amplifier 44 is fed via line 57 to a voltage comparator 58 in which it is compared with a reference voltage manually preset at 60. If the voltage on line 57 exceeds the reference, indicating a defect greater than a selected size, an output signal is provided via amplifier 62 to drive for example a visual warning such as L.E.D. 64, an audio alarm 66, or an output peripheral such as a chart recorder via output 68.

The probe described above has been developed particularly (but not exclusively) for the underwater inspection of welds in ferrous metal in "as welded" condition, i.e. with no prior surface grinding or preparation. Such inspection poses a number of problems, particularly (a) the weld surface is rough, typically with a variation of up to 4 mm, which produces probe current variations arising from the varying distance of the probe from the bulk metal ("lift-off")

(b) cracks to be detected may be significantly smaller than the surface roughness of the weld (c) the cracks may be in any orientation with respect to the weld; it is particularly difficult to detect a crack running along the weld when traversing the probe along the weld.

The probe described above is of utility in meeting these problems for the following reasons.

A high intensity of eddy current field is obtained by positioning the coils close to the front face of the probe, by the use of the ferrite core, by the provision of high impedance coils using enamelled copper wire, and by the choice of frequency. The high intensity field thus induced gives a high sensitivity.

The use of twin balanced coils permits easy use on common ferrous materials since variations in magnetic permeability and eddy current intensity affects both the primary and secondary coils and can be balanced out.

These factors together with a small coil diameter and the spatial arrangement of the coils have been found to give a high flaw resolution and to fully detect defects at all directions to the line of probe movement.

Figure 5:
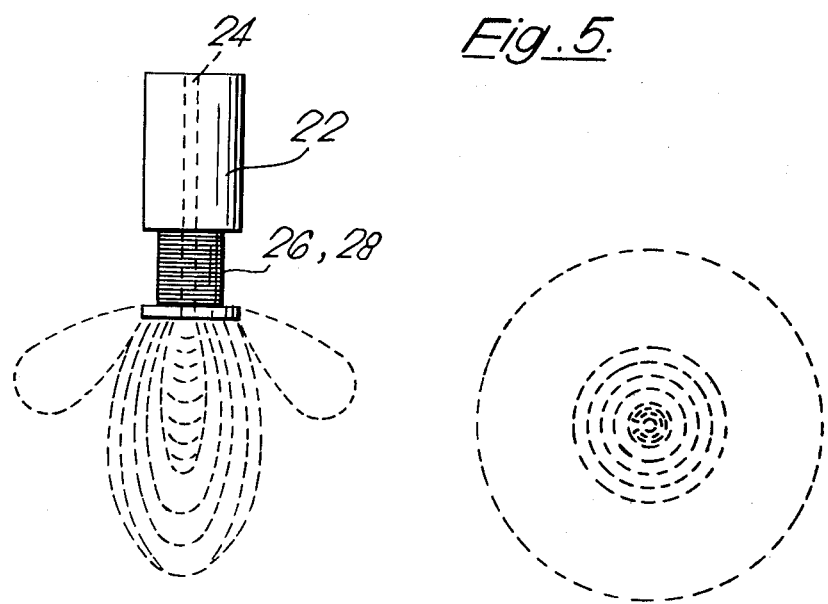
FIG. 5 is a diagrammatic representation of the flux field concentration produced by the probe.

FIG. 5 represents a typical pattern of flux field concentration for the probe. It will be seen that a highly concentrated field is obtained which has a high intensity columnar central portion. This permits defects to be detected even when there is a large amount of lift-off, typically up to 6 mm.

One other major advantage of the present probe is that it distinguishes between signal changes caused by lift-off and those caused by cracks, there being a clear 90° phase discrimination.

Thus the probe provides for the speedy and simple inspection of ferrous welds in as-welded condition.

The above embodiment is exemplary only, and modifications may be made within the scope of the claims. For example, the circuit of FIG. 6 may be replaced by a digitally based system in which the output of the bridge is digitised and thereafter processed by logic circuits or a microprocessor.

I claim:

1. An eddy current inspection probe comprising a ferrite rod, a non-conductive bobbin located on the ferrite rod and having a coil-receiving portion positioned adjacent one end of the ferrite rod and two coils wound around the rod axis in said coil-receiving portion, each coil having a first full layer of turns extending along the whole of said coil-receiving portion and a second partial layer of turns, the two said partial layers froming a common layer sandwiched between said first layers.

2. The probe of claim 1, in which the bobbin is plastic and has a central bore in which the ferrite rod is received.

3. The probe of claim 1, in which the bobbin is mounted within a waterproof housing.

4. The probe of claim 1, in which the coils are of enamelled copper wire.

5. Eddy current inspection apparatus, including the probe of claim 1 in combination with:
impedance means connected with said coils to form an a.c. bridge circuit;
oscillator means connected to drive said bridge circuit;
a signal detector connected to receive the output of said bridge circuit and operative to generate from the bridge circuit output at least a first signal representing the phase difference between the bridge circuit output and the signal driving the bridge circuit; and
output means providing a defect signal in dependence on said first signal.

6. The apparatus of claim 5, in which the signal detector is operative also to provide a second signal which is a function of the voltage of the bridge output signal; and in which the output means includes an oscilloscope having one direction of deflection controlled by said first signal and the other direction of deflection controlled by said second signal.

7. The apparatus of claim 5, in which said first signal is applied to a level detector having an output connected to drive an alarm.

8. The apparatus of claim 7, including means for manually setting a reference level for the level detector.

9. The apparatus of claim 5, in which the oscillator means operates at a frequency between 1.5 MHz and 2.0 MHz.

* * * * *